United States Patent
Petersen

(10) Patent No.: US 9,642,576 B2
(45) Date of Patent: *May 9, 2017

(54) CANCELLATION OF LIGHT SHUNTING

(71) Applicant: COVIDIEN LP, Mansfield, MA (US)

(72) Inventor: Ethan Petersen, Castro Valley, CA (US)

(73) Assignee: Covidien LP, Mansfield, MA (US)

(*) Notice: Subject to any disclaimer, the term of this patent is extended or adjusted under 35 U.S.C. 154(b) by 335 days.

This patent is subject to a terminal disclaimer.

(21) Appl. No.: 14/565,059

(22) Filed: Dec. 9, 2014

(65) Prior Publication Data

US 2015/0087939 A1 Mar. 26, 2015

Related U.S. Application Data

(63) Continuation of application No. 13/589,642, filed on Aug. 20, 2012, now Pat. No. 8,923,944, which is a continuation of application No. 11/716,978, filed on Mar. 9, 2007, now Pat. No. 8,265,724.

(51) Int. Cl.
A61B 5/1455 (2006.01)
A61B 5/00 (2006.01)
A61B 5/1495 (2006.01)
G01D 5/30 (2006.01)
G01D 18/00 (2006.01)
A61B 5/145 (2006.01)
A61B 90/90 (2016.01)
A61B 90/98 (2016.01)

(52) U.S. Cl.
CPC .......... *A61B 5/7203* (2013.01); *A61B 5/1495* (2013.01); *A61B 5/14546* (2013.01); *A61B 5/14551* (2013.01); *A61B 5/14552* (2013.01); *A61B 5/7225* (2013.01); *A61B 5/7278* (2013.01); *A61B 5/742* (2013.01); *A61B 90/90* (2016.02); *A61B 90/98* (2016.02); *G01D 5/30* (2013.01); *G01D 18/008* (2013.01); *A61B 2560/0233* (2013.01); *A61B 2562/085* (2013.01); *Y10T 29/49002* (2015.01)

(58) Field of Classification Search
CPC ... A61B 5/0002; A61B 5/0059; A61B 5/1455; A61B 5/14551; A61B 5/14552
See application file for complete search history.

(56) References Cited

U.S. PATENT DOCUMENTS

| 4,621,643 | A | 11/1986 | New, Jr. et al. |
| 4,700,708 | A | 10/1987 | New, Jr. et al. |
| 4,770,179 | A | 9/1988 | New, Jr. et al. |
| 4,796,636 | A | 1/1989 | Branstetter et al. |

(Continued)

FOREIGN PATENT DOCUMENTS

| CN | 1540314 | 10/2004 |
| EP | 1828731 | 9/2007 |

(Continued)

Primary Examiner — Eric Winakur
Assistant Examiner — Chu Chuan (JJ) Liu
(74) Attorney, Agent, or Firm — Fletcher Yoder, P.C.

(57) ABSTRACT

There is provided a system and method for canceling shunted light. The method includes transmitting electromagnetic radiation at tissue of interest and generating a signal representative of detected electromagnetic radiation. A portion of the generated signal representing shunted light is canceled from the generated signal and the remaining portion of the generated signal is used to compute physiological parameters.

20 Claims, 4 Drawing Sheets

(56) References Cited

U.S. PATENT DOCUMENTS

| | | |
|---|---|---|
| 4,913,150 A | 4/1990 | Cheung et al. |
| 4,942,877 A | 7/1990 | Sakai et al. |
| 5,058,588 A | 10/1991 | Kaestle |
| 5,278,627 A | 1/1994 | Aoyagi et al. |
| 5,348,005 A | 9/1994 | Merrick |
| 5,660,567 A | 8/1997 | Nierlich et al. |
| 5,685,301 A | 11/1997 | Klomhaus |
| 5,758,644 A | 6/1998 | Diab et al. |
| 5,783,821 A | 7/1998 | Costello, Jr. |
| 5,797,841 A | 8/1998 | Delonzor et al. |
| 5,823,950 A | 10/1998 | Diab et al. |
| 5,922,607 A | 7/1999 | Bernreuter |
| 5,924,982 A | 7/1999 | Chin |
| 5,995,855 A | 11/1999 | Kiani et al. |
| 6,011,986 A | 1/2000 | Diab et al. |
| 6,078,833 A | 6/2000 | Hueber |
| 6,133,994 A | 10/2000 | Yamanishi et al. |
| 6,349,228 B1 | 2/2002 | Kiani et al. |
| 6,377,829 B1 | 4/2002 | Al-Ali |
| 6,397,091 B2 | 5/2002 | Diab et al. |
| 6,549,284 B1 | 4/2003 | Boas |
| 6,553,241 B2 | 4/2003 | Mannheimer et al. |
| 6,580,086 B1 | 6/2003 | Schulz et al. |
| 6,584,336 B1 | 6/2003 | Ali et al. |
| 6,591,123 B2 | 7/2003 | Fein et al. |
| 6,597,933 B2 | 7/2003 | Murayama et al. |
| 6,600,940 B1 | 7/2003 | Fein et al. |
| 6,606,510 B2 | 8/2003 | Swedlow et al. |
| 6,628,975 B1 | 9/2003 | Fein et al. |
| 6,725,075 B2 | 4/2004 | Al-Ali |
| 6,852,083 B2 | 2/2005 | Caro et al. |
| 6,865,407 B2 | 3/2005 | Kimball et al. |
| 6,882,874 B2 | 4/2005 | Huiku |
| 6,889,153 B2 | 5/2005 | Dietiker |
| 6,898,452 B2 | 5/2005 | Al-Ali et al. |
| 6,950,687 B2 | 9/2005 | Al-Ali |
| 6,997,880 B2 | 2/2006 | Carlebach et al. |
| 6,999,904 B2 | 2/2006 | Weber et al. |
| 7,039,449 B2 | 5/2006 | Al-Ali |
| 7,047,055 B2 | 5/2006 | Boas |
| 7,120,480 B2 | 10/2006 | Chew et al. |
| 7,124,048 B2 | 10/2006 | Dietiker |
| 7,142,901 B2 | 11/2006 | Kiani et al. |
| 7,215,985 B2 | 5/2007 | Petersen et al. |
| 7,239,901 B2 | 7/2007 | Gritsenko |
| 7,272,425 B2 | 9/2007 | Al-Ali |
| 7,274,955 B2 | 9/2007 | Kiani et al. |
| 7,349,726 B2 | 3/2008 | Casciani et al. |
| 7,350,919 B2 | 4/2008 | Hillis et al. |
| 7,373,192 B2 | 5/2008 | Chew et al. |
| 7,376,454 B2 | 5/2008 | Casciani et al. |
| 7,428,432 B2 | 9/2008 | Al-Ali et al. |
| 7,438,683 B2 | 10/2008 | Al-Ali et al. |
| 7,460,909 B1 | 12/2008 | Koh et al. |
| 8,000,760 B2 | 8/2011 | Mannheimer et al. |
| 2002/0082489 A1 | 6/2002 | Casciani et al. |
| 2002/0103423 A1 | 8/2002 | Chin et al. |
| 2003/0176776 A1 | 9/2003 | Huiku |
| 2003/0195402 A1 | 10/2003 | Fein et al. |
| 2003/0197679 A1 | 10/2003 | Al-Ali et al. |
| 2004/0133088 A1 | 7/2004 | Al-Ali |
| 2004/0147823 A1 | 7/2004 | Tanaka et al. |
| 2004/0147824 A1 | 7/2004 | Diab et al. |
| 2004/0162472 A1 | 8/2004 | Berson et al. |
| 2004/0242980 A1 | 12/2004 | Kiani et al. |
| 2004/0267103 A1 | 12/2004 | Li et al. |
| 2005/0065417 A1 | 3/2005 | Al-Ali et al. |
| 2005/0168722 A1 | 8/2005 | Forstner et al. |
| 2005/0197551 A1 | 9/2005 | Al-Ali et al. |
| 2005/0222502 A1 | 10/2005 | Cooper |
| 2005/0250998 A1 | 11/2005 | Huiku |
| 2006/0020185 A1 | 1/2006 | Al-Ali |
| 2006/0030763 A1 | 2/2006 | Mannheimer et al. |
| 2006/0195026 A1 | 8/2006 | Casciani et al. |
| 2006/0195027 A1 | 8/2006 | Casciani et al. |
| 2006/0200018 A1 | 9/2006 | Al-Ali |
| 2006/0211925 A1 | 9/2006 | Lamego et al. |
| 2006/0211929 A1 | 9/2006 | Casciani et al. |
| 2006/0217604 A1 | 9/2006 | Fein et al. |
| 2006/0217605 A1 | 9/2006 | Fein et al. |
| 2006/0217606 A1 | 9/2006 | Fein et al. |
| 2006/0217607 A1 | 9/2006 | Fein et al. |
| 2006/0217608 A1 | 9/2006 | Fein et al. |
| 2006/0224059 A1 | 10/2006 | Swedlow |
| 2006/0229510 A1 | 10/2006 | Fein et al. |
| 2006/0229511 A1 | 10/2006 | Fein et al. |
| 2006/0253007 A1 | 11/2006 | Cheng et al. |
| 2006/0258923 A1 | 11/2006 | Al-Ali et al. |
| 2006/0258924 A1 | 11/2006 | Al-Ali et al. |
| 2006/0258925 A1 | 11/2006 | Al-Ali et al. |
| 2006/0258926 A1 | 11/2006 | Al-Ali et al. |
| 2006/0270920 A1 | 11/2006 | Al-Ali et al. |
| 2006/0281983 A1 | 12/2006 | Al-Ali et al. |
| 2007/0043269 A1 | 2/2007 | Mannheimer et al. |
| 2007/0043270 A1 | 2/2007 | Mannheimer et al. |
| 2007/0043271 A1 | 2/2007 | Mannheimer et al. |
| 2007/0043272 A1 | 2/2007 | Mannheimer et al. |
| 2007/0043273 A1 | 2/2007 | Mannheimer et al. |
| 2007/0043274 A1 | 2/2007 | Mannheimer et al. |
| 2007/0043275 A1 | 2/2007 | Mannheimer et al. |
| 2007/0043276 A1 | 2/2007 | Mannheimer et al. |
| 2007/0043277 A1 | 2/2007 | Mannheimer et al. |
| 2007/0043278 A1 | 2/2007 | Mannheimer et al. |
| 2007/0043279 A1 | 2/2007 | Mannheimer et al. |
| 2007/0043280 A1 | 2/2007 | Mannheimer et al. |
| 2007/0043282 A1 | 2/2007 | Mannheimer et al. |
| 2007/0049810 A1 | 3/2007 | Mannheimer et al. |
| 2007/0073127 A1 | 3/2007 | Kiani et al. |
| 2007/0088207 A1 | 4/2007 | Mannheimer et al. |
| 2007/0100220 A1 | 5/2007 | Baker, Jr. |
| 2007/0112260 A1 | 5/2007 | Diab et al. |
| 2007/0208236 A1 | 9/2007 | Hicks |
| 2007/0225614 A1 | 9/2007 | Naghavi et al. |
| 2007/0244376 A1 | 10/2007 | Wang |
| 2008/0015424 A1 | 1/2008 | Bernreuter |
| 2008/0039701 A1 | 2/2008 | Al-Ali et al. |
| 2008/0221427 A1 | 9/2008 | Petersen |

FOREIGN PATENT DOCUMENTS

| | | |
|---|---|---|
| JP | 24113353 | 4/2004 |
| JP | 27330708 | 12/2007 |
| WO | 9526676 | 10/1995 |
| WO | 9817174 | 4/1998 |
| WO | 0214793 | 2/2002 |
| WO | 2008035076 | 3/2008 |

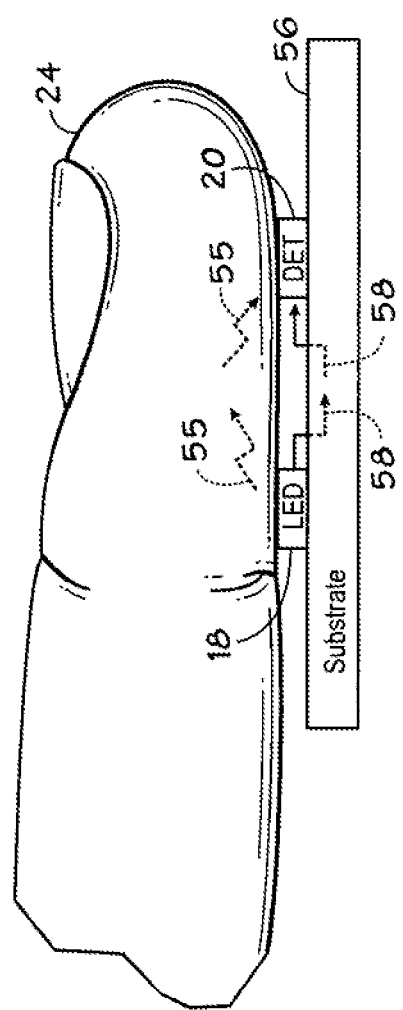

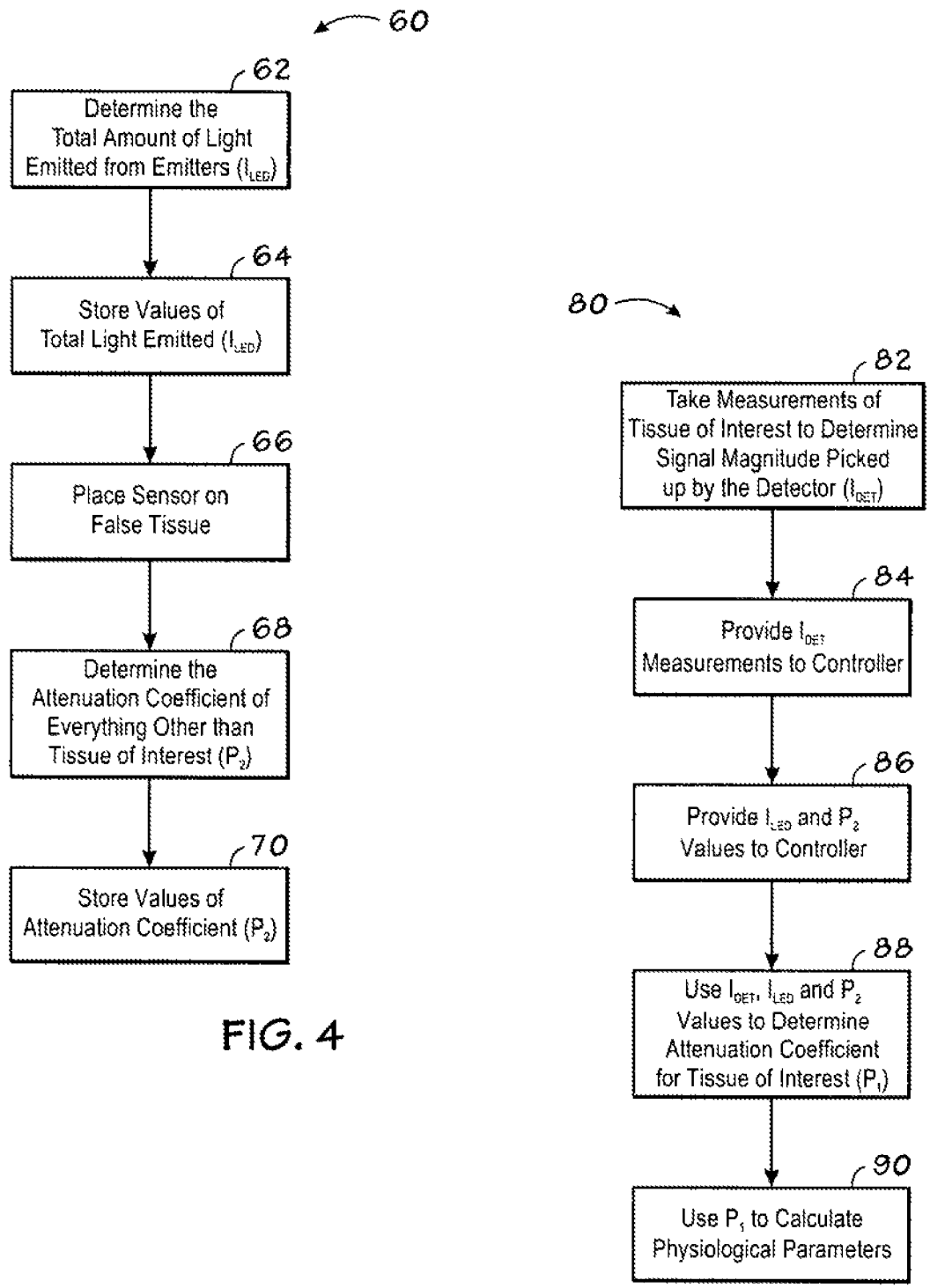

CANCELLATION OF LIGHT SHUNTING

CROSS-REFERENCE TO RELATED APPLICATIONS

This application is a continuation of U.S. application Ser. No. 13/589,642, filed Aug. 20, 2012, entitled "CANCELLATION OF LIGHT SHUNTING," which is a continuation of U.S. application Ser. No. 11/716,978, filed Mar. 9, 2007, entitled "CANCELLATION OF LIGHT SHUNTING," the full disclosures of which are incorporated by reference herein in their entirety.

TECHNICAL FIELD

The present invention relates generally to medical devices and, more particularly, to medical devices for non-invasively measuring physiological parameters of a patient.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other health care personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heart beat of a patient. In fact, the "pulse" in pulse oximetry refers to the time varying amount of arterial blood in the tissue during each cardiac cycle.

Pulse oximeters typically utilize a non-invasive sensor that transmits electromagnetic radiation, such as light, through a patient's tissue and then photo-electrically detects the absorption and scattering of the transmitted light in such tissue. One or more of the above mentioned physiological characteristics may then be calculated based upon the amount of light absorbed and scattered. More specifically, the light passed through the tissue is typically selected to be of one or more wavelengths that may be absorbed and scattered by the blood in an amount correlative to the amount of blood constituent present in the tissue. The measured amount of light absorbed and scattered may then be used to estimate the amount of blood constituent in the tissue using various algorithms.

The pulse oximetry measurement depends in part on an assumption that the contribution of detected light that has not passed through a patient's tissue is negligible. This assumption, however, may not be accurate. Specifically, light shunting may occur, wherein light transmitted from an emitter in the sensor may arrive at a detector without first having traveled through the patient's tissue. The light shunting may cause measurement variations that do not relate to the amount of blood constituent and, therefore, may lead to inaccurate measurements.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In accordance with one aspect of the present invention, there is provided a method of manufacture for a non-invasive sensor. The method includes providing a sensor communicatively coupled to a monitor, wherein the sensor is configured to emit and detect electromagnetic radiation. The method also includes determining a first signal value for each wavelength of light emitted from an emitter of the sensor and storing the first signal value in a memory. Additionally, the method includes placing false tissue on the sensor, operating the sensor to determine a second signal value for each wavelength emitted from the emitter of the sensor and storing the second signal value in the memory.

In accordance with another aspect of the present invention, there is provided a method for operating a system for non-invasively determining physiological parameters. The method includes using a sensor to take measurements of tissue of interest and providing the measurements to a controller in a monitor. Additionally, first and second values are retrieving from memory, the first value representing an amount of light emitted from emitters in the sensor and the second value representing an attenuation coefficient of everything other than the tissue of interest. A third value representing an attenuation coefficient for the tissue of interest is determined using the measurements provided to the controller and the first and second values. The third value is used to calculate physiological parameters.

In accordance with yet another aspect of the present invention, there is provided a system comprising a sensor and a monitor. The sensor includes an emitter configured to emit electromagnetic radiation at tissue and a detector configured to generate a signal in response to detecting the electromagnetic radiation emitted from the emitter. The monitor is communicatively coupled with the sensor and includes a controller configured to remove a shunting light value from the generated signal to produce an attenuation coefficient of the tissue. The monitor is configured to use the attenuation coefficient in calculating physiological parameters.

BRIEF DESCRIPTION OF THE DRAWINGS

Certain exemplary embodiments are described in the following detailed description and in reference to the drawings in which:

FIG. 3 illustrates possible light pathways for light to arrive at a detector from an emitter in the system of FIG. 1 in accordance with an exemplary embodiment of the present invention;

FIG. 4 is a flow chart illustrating a technique for calibrating the system of FIG. 1 in accordance with an exemplary embodiment of the present invention; and FIG. 5 is a flow chart representation of a method for canceling the effects of light shunting in the system of FIG. 1 in accordance with an exemplary embodiment of the present invention.

DETAILED DESCRIPTION

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In accordance with the present techniques, a system and method are provided for canceling shunted light. The method includes determining and storing a value representative of an amount of shunted light. The stored value is subsequently used to cancel all or a portion of the shunted light from a detected signal. The method may be implemented in systems using photoelectric sensors, such as pulse oximeters for example.

Figure 1:
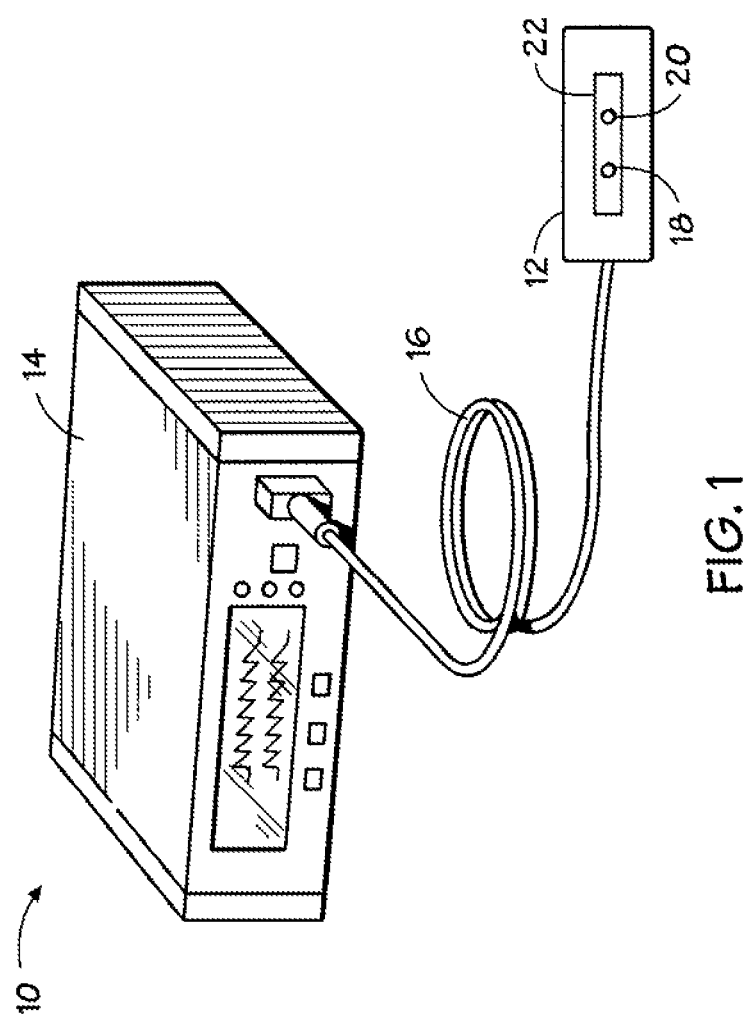
FIG. 1 illustrates a system for non-invasively determining physiological parameters in accordance with an exemplary embodiment of the present invention.

Turning to FIG. 1, a system for non-invasively determining physiological parameters is illustrated in accordance with an exemplary embodiment of the present invention and is generally designated by the reference numeral 10. The system 10 includes a sensor 12 coupled with a monitor 14 via a cable 16. The sensor 12 includes an emitter 18 and a detector 20. The emitter 18 may include one or more electromagnetic radiation sources such as a light emitting diodes (LEDs), an array of LEDs, a white light source, a tunable laser, or any other source that transmits electromagnetic radiation within a region of the electromagnetic spectrum useful for the determination of physiological parameters. The detector 20 may be a photosensitive diode, photosensitive transistor or other means for detecting electromagnetic radiation. The detector 20 is configured to detect electromagnetic radiation originating from the emitter 18.

The sensor 12 may be either a transmission-type sensor or a reflection-type sensor. In a transmission-type sensor, the sensor's emitter and detector lie on opposing sides of the tissue when the sensor is applied to a patient. The optical path of the light originating from the emitter 18 is substantially in-line with an imaginary axis connecting the emitter 18 and the detector 20. For reflectance-type sensors, the optical path is somewhat more complicated, as the light first enters perfused tissue and then is scattered back to the detector 20. In an exemplary embodiment, the sensor 12 is a reflectance type sensor, and the detector 20 and emitter 18 are mounted on a circuit board 22. Mounting the emitter 18 and the detector 20 on the same circuit board 22 allows for a constant geometric orientation between the emitter 18 and detector 20 to be maintained. For example, the circuit board 22 maintains the emitter 18 and detector 20 at a controlled optical distance relative to each other. The controlled optical distance reduces the amount of variance of light shunting during iterative measurements, to facilitate the approximation of and subsequent cancellation of the shunted light, as will be discussed in greater detail below.

Figure 2:
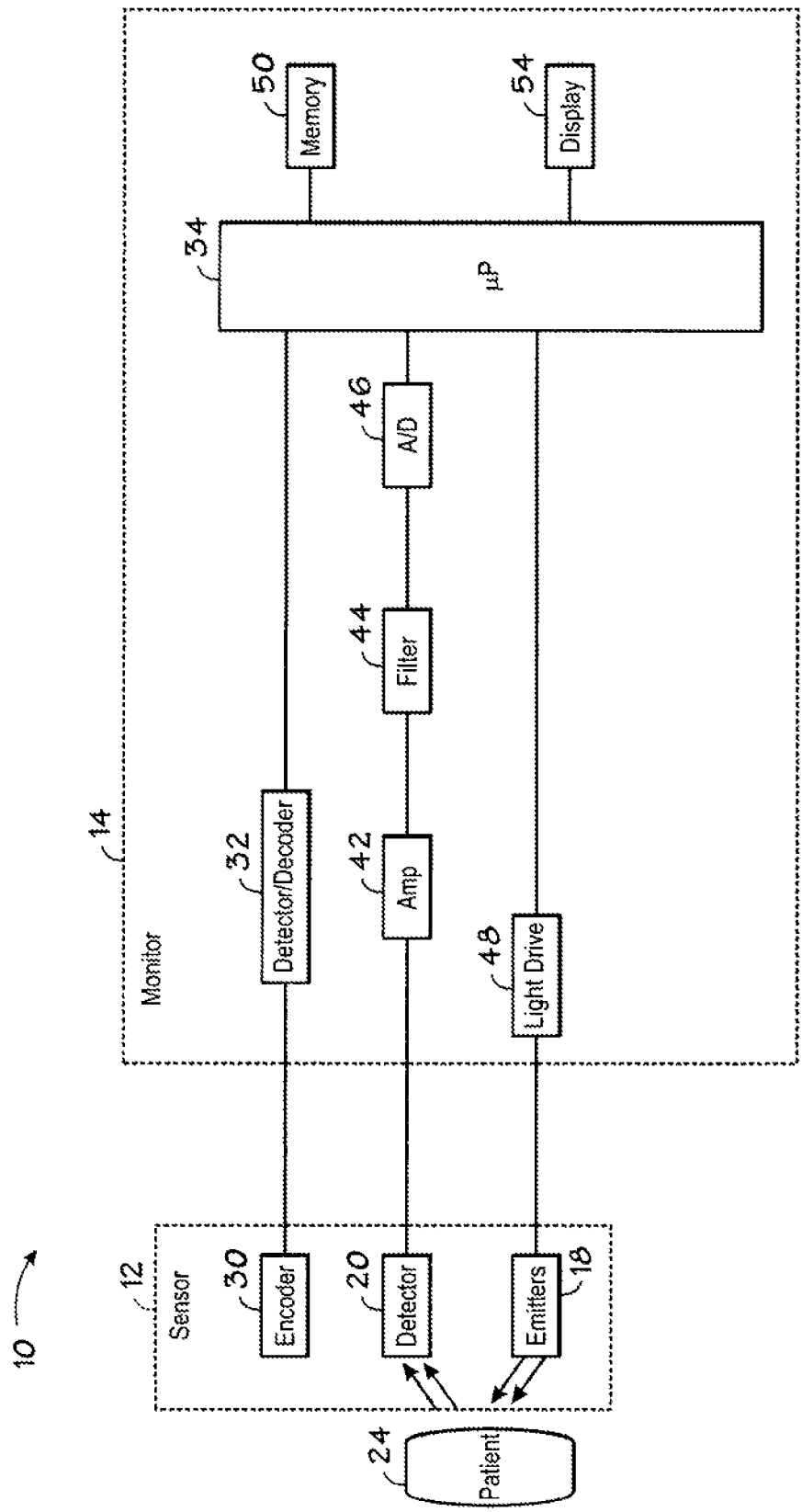
FIG. 2 is a block diagram of a sensor and a monitor of the system illustrated in FIG. 1 in accordance with an exemplary embodiment of the present invention.

Referring to FIG. 2, a block diagram of the system 10 of FIG. 1 is illustrated in accordance with an exemplary embodiment of the present invention. As can be seen, the sensor is configured so that the detector 20 receives light originating from the emitter 18 after it has passed through a patient's tissue 24. Additionally, the sensor 12 includes an encoder 30, which that may be a resistor having a value representative of operating characteristics of the sensor 12. In an alternative embodiment, the encoder 30 may be a memory device such as random access memory (RAM), a flash memory, a programmable read only memory (PROM), or an electrically erasable programmable read only memory (EEPROM), for example, configured to store values related to the shunting characteristics of the sensor 12. For example, the encoder 30 may store constants or coded values related to light shunting. Additionally, the encoder may be configured to store other parameters related to the particular sensor being used, such as the particular wavelengths at which the emitter 18 is operating, for example. As discussed in greater detail below, the stored constants or coded values may be used to cancel shunted light in order to achieve a more accurate measurement of the amount of light attenuation resulting from the tissue of interest.

The encoder 30 may be communicatively coupled to the monitor 14 in order to communicate the constant or coded values to a detector/decoder 32 in the monitor 14. The detector/decoder 32 is provided for reading the constants or coded values from the encoder 30 in the sensor 12. If the encoder stores constants, the constants may be provided directly to a controller 34 from the detector/decoder 32. Alternatively, if coded values are used, the detector/decoder 32 may correlate the coded values to constants using a look up table (not shown). In such a configuration, the look-up table may be configured to provide the corresponding constants to the controller 34.

The controller 34 may be a microprocessor configured to compute physiological parameters using algorithms known in the art. The constants are provided to the controller 34 for the determination of the amount of detected light that passed through the patient's tissue 24 during operation of the system 10. Specifically, the constants are used to remove an amount of shunted light from a detected signal so that the determination of physiological parameters does not include the shunted light, as will be discussed in greater detail below.

During use of the system 10, the controller 34 receives a signal representing the total amount of light detected from the sensor 12. This signal originates from the detector 20 generating an electrical current in response to the total light detected from the emitter 18, i.e., light that has passed through the tissue 24 and shunted light, and provides the generated signal to the monitor 14 for processing. The monitor 14 amplifies (amplifier 42) and filters (filter 44) the signal before converting (converter 46) the signal to a digital signal. The digital signal is provided to the controller 34 and used in conjunction with the stored constants discussed above to determine the amount of light attenuation of the tissue of interest. Once the light attenuation of the tissue of interest is calculated, by removing the shunted light from the detected signal, it may be used in computing the various physiological parameters in accordance with algorithms known in the art.

As illustrated in FIG. 2, additional component parts of the monitor 14 may include a light drive 48, a memory device 50, and a display 54. The light drive 48 drives the emitters 18 and the display 54 displays the physiological parameters once they are computed. The memory device 50 may be used to store the algorithms used in computing physiological parameters.

To demonstrate the effects of light shunting, a reflectance type sensor is illustrated in FIG. 3. Specifically, two possible pathways by which the light may travel from the emitter 18 to arrive at the detector 20 are illustrated. Ideally, all of the electromagnetic radiation from the emitter 18 arrives at the detector 20 after having passed through the tissue of interest 24, as indicated by the arrows 55. However, in practice, some of the light from the emitter 18 may be shunted through the circuit board 56 and may be detected by the detector 20 without having passed through the tissue of interest 24, as indicated by the arrows 58. The detected light that does not pass through the tissue of interest 24, i.e., the shunted light indicated by the arrows 58, may cause measurement errors in the parameters, e.g., oxygen saturation, calculated by the monitor 14.

For example, in one embodiment, the system 10 implemented may be an oximeter with a first light signal operating in the red region of the electromagnetic spectrum and the second light signal in the infrared region of the electromagnetic spectrum. The detected light signals are conditioned and processed to determine AC and DC signal components. Once obtained, the AC and DC components may be used to compute a modulation ratio of the red to infrared signals. The modulation ratio is generally referred to as "the ratio of ratios," or "Ratrat," and may be represented as:

$$Ratrat = \frac{AC_{Rd}/DC_{Rd}}{AC_{IR}/DC_{IR}}. \tag{1}$$

The Ratrat is used to calculate physiological parameters in accordance with algorithms known in the art. Among other things, shunted light causes the DC terms of a Ratrat equation to be artificially high. Accordingly, removal of the shunted light will help increase the accuracy of the parameters calculated based on signals received from the sensor 12.

To determine the amount of shunted light for a particular sensor, several parameters of the particular sensor or sensor family can be evaluated. The parameters may include, for example, the signal magnitude emitted from the emitter 18 and the signal magnitude detected by the detector 20. The signal magnitude detected by the detector 20 while the sensor 12 is in service represents the sum of the light that passed through the tissue of interest 24 and the shunted light. As such, the total light detected by the detector 20 can be represented by:

$$I_{DET} = I_{LED}P_1 + I_{LED}P_2, \tag{2}$$

where $I_{DET}$ represents the signal magnitude picked up by the detector, and $I_{LED}$ represents the signal magnitude from the emitters 18. $P_1$ represents the attenuation coefficient of the tissue of interest, as discussed above, and resulting from light traversing tissue as shown by arrows 55 in FIG. 3. $P_2$ represents the attenuation coefficient of everything other than the tissue of interest resulting from shunted light, as shown by arrows 58 in FIG. 3. The parameter that system 10 may use in determining physiological parameters is $P_1$, the attenuation of the tissue of interest or the attenuation coefficient of light in a capillary bed. Once the $P_1$ value has been determined, the AC and DC values of the Ratrat equation (1) may be determined based on the $P_1$ value. Accordingly, equation (2) may be rearranged to solve for $P_1$.

$$P_1 = \frac{I_{DET} - I_{LED}P_2}{I_{LED}}. \tag{3}$$

The value of $P_2$ can be determined by taking measurements of only the shunted light before the sensor is placed into service. A flow chart illustrating a technique 60 for use in determining an amount of light shunting ($P_2$) for the system 10 of FIG. 1 is shown in accordance with an exemplary embodiment of the present invention. The technique 60 may be used during the manufacture or testing of the system 10 or, alternatively, prior to the manufacture of the system 10. Additionally, the technique 60 may be performed for each sensor or for each type of sensor depending on the controls of the manufacturing process involved. For example, if the controls are tight, meaning there is only slight variance between sensors, then the technique may be performed on only a small sample size of sensors and the results may be reasonably accurate for all other sensors of that type.

The technique 60 begins with a determination of the total amount of light emitted from the emitters ($I_{LED}$), as indicated at block 62. The determined $I_{LED}$ values are then stored, as indicated at block 64. The attenuation coefficient of everything other than the tissue of interest ($P_2$) is then determined by placing false tissue on the sensor and taking measurements, as indicated at blocks 66 and 68. The $P_2$ values are stored for later use in canceling the light shunting from a measured signal, as indicated at block 70. The $P_2$ signal measured at the detector while the false tissue is in place represents the amount of shunted light for that sensor.

The technique 60 may be performed using a testing device (not shown) configured to operate the sensor 12 to determine the various operating parameters. The false tissue may be a false finger or other tissue phantom, made of black foam or black Acrylonitrile Butadiene Styrene (ABS) plastic, for example. The false tissue should be opaque so that it does not allow light that has been directed into it from the emitter 18 to be reflected back to the detector 20. Specifically, the false tissue should absorb the light that impinges on it so that any signal detected by the detector 20 may be attributed to shunting. More sophisticated embodiments of false tissue are possible. For instance, the surface of the false tissue could have optical properties similar to real tissue so that light reflected off the surface is reflected back into the sensor substrate and is included in the shunted light measurement.

As mentioned above, a small sample size for a given type of sensor may be representative of all sensors of that type such that averaged $P_2$ and $I_{LED}$ values from the samples may be used in all sensors of that particular type having the same particular configuration, thus saving resources during manufacturing. Specifically, as the actual amount of light shunting that occurs while using a particular sensor may vary from user-to-user, exactness in the $P_2$ and $I_{LED}$ values for that particular sensor is not necessary. Indeed, averaged $P_2$ and $I_{LED}$ values provide adequate cancellation of shunted light to allow for increased accuracy in measurements. As such, an average $P_2$ and $I_{LED}$ values can be representative for an entire type or family of sensors. In this situation, where $P_2$ values are provided based on sensor type, the monitor 14 can store the values for each type of sensor without reading values from each sensor. As discussed above, the monitor may recognize a sensor when the sensor is coupled to the monitor, so the monitor can automatically retrieve the appropriate constants for cancellation of the shunted light.

The approximation of light shunting should be performed separately for each wavelength of light at which measurements are to be taken. For example, for a sensor having LEDs operating in both the red region the infrared region of the electromagnetic spectrum, the calculation may be done separately for each LED and a $P_2$ value is determined for each LED.

The constants or coded values stored on the sensor 12 or the monitor 14 related to shunted light may include the $P_2$ and $I_{LED}$ values. The parameter $I_{DET}$ is determined during operation of the sensor 12 and the parameter $P_1$ is calculated in accordance with equation (3). $I_{LED}$ values may also be determined during operation, so that only the $P_2$ values are stored in memory prior to operation of the sensor. $I_{LED}$ values are usually controlled by the instrument to adapt to differences between different patients. There is usually a large variation in optical properties from one patient to the next, so the light output of the emitters is adjusted by the instrument in order to keep the signal at the detector within a useful range. The calculated $P_1$ values, once determined, may be used for calculating physiological parameters in accordance with algorithms known in the art.

It should be understood that the amount of shunting that actually occurs may depend on many factors, one of which is the type of sensor being used. An estimation of the amount of shunted light is sufficiently accurate as long as the sensor materials and the optical distance between the emitter 18 and detector 20 remain relatively constant (i.e. controlled optical distance). Specifically, although there may be variance in the amount of shunted light due to patient specific factors, variation in the amount of shunted light resulting from sensor specific factors can be limited by limiting variance from one sensor to another for a particular sensor type.

Additionally, the amount of light shunting may vary among various sensors. Indeed, particular sensors may be more susceptible to shunting. For example, sensors implementing a white bandage to secure the sensor 12 to the tissue of interest, or sensors where the circuit board 22 is translucent, may be especially vulnerable to shunting. Furthermore, for example, if the material used to manufacture a particular type of sensor changes, the amount of shunted light may change and the constant or coded values may no longer be accurate. As such, the above mentioned $P_2$ parameter will vary according to each specific sensor design and values should be determined for each particular sensor design.

As mentioned above, the estimated amount of shunted light can be stored as a constant or as a coded value in the encoder 30 of the sensor 12 shown in FIG. 2. The constant or coded value may be communicated to the monitor 14 when the sensor 12 is used in conjunction with a monitor 14. The communication of constants or coded values from a sensor to a monitor is described in U.S. Pat. No. 6,628,975, which is incorporated herein by reference. In an alternative embodiment, the constant or coded values may be stored in a look-up table of the monitor 14. The sensor 12 communicates the coded values to the monitor 14 and the coded values are correlated with the appropriate constants stored in the look-up table. In yet another alternative embodiment, the monitor 14 may store constants for multiple sensor types and upon coupling of the sensor 12 to the monitor 14, the monitor 14 determines what particular sensor is being used and retrieves the corresponding constants for that particular sensor.

As described above, the constants and/or coded values are used to indicate a shunted light value that is representative of the amount of shunted light that can be expected to occur for a particular sensor or for a particular sensor type. Knowing the amount of shunted light, the monitor 14 can remove the shunted light from the detected light signal to determine the amount of light attenuation of the tissue of interest ($P_1$ values). The $P_1$ values can then be used to in determining the AC and DC values representative of only the portion of the detected signal that can be attributed to light that has traversed the tissue of interest.

Turning to FIG. 5, a flow chart representation of a technique 80 for cancellation of light shunting during operation of the system 10 of FIG. 1 is illustrated. The technique 80 includes taking measurements of tissue using the noninvasive sensor 12 to determine the signal magnitude picked up by the detector ($I_{DET}$), as indicated at block 82. The $I_{DET}$ measurements are provided to the controller 38, as indicated at block 84. The stored values, $I_{LED}$ and $P_2$, are provided to the controller 38, as indicated at block 86. The $I_{DET}$, $I_{LED}$, and $P_2$ values are then used to determine the attenuation coefficient for tissue of interest ($P_1$), as indicated at block 88, by canceling the shunted light using equation (3). Physiological parameters may then determined using the value $P_1$, as indicated at block 90. Specifically, in the case of a pulse oximeter, the Ratrat may be determined using the $P_1$ values to determine the AC and DC parts of the detected signal.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A monitor, comprising:
   a memory device comprising one or more tangible, non-transitory, machine readable media collectively storing one or more sets of instructions; and
   a processing device configured to execute the one or more sets of instructions to:
   retrieve a first value representative of a total amount of light emitted by an emitter disposed on a sensor communicatively coupled to the monitor when the sensor is disposed on a tissue of interest;
   receive a signal generated by a detector disposed on the sensor, wherein the signal is representative of a first amount of light detected by the detector;
   retrieve a second value from the memory device or the sensor, wherein the second value is a first attenuation coefficient representative of a second amount of light shunting through the sensor;
   determine a third value based at least in part on the first value, the second value, and the first amount of light, wherein the third value is a second attenuation coefficient representative of the tissue of interest; and
   determine a physiological parameter based at least in part on the third value.

2. The monitor of claim 1, wherein determining the third value based at least in part on the first value and the second value comprises removing the second amount of light shunting through the sensor from the first amount of light detected by the detector.

3. The monitor of claim 1, wherein determining the physiological parameter based at least in part on the third value comprises using the equation $$P_1 = \frac{I_{DET} - I_{LED}P_2}{I_{LED}},$$

wherein $I_{LED}$ is the first value, $P_2$ is the second value, $I_{DET}$ is the first amount of light detected by the detector, and $P_1$ is the third value.

4. The monitor of claim 1, wherein the one or more sets of instructions identify a type of sensor or the individual sensor communicatively coupled to the monitor.

5. The monitor of claim 4, wherein the one or more sets of instructions receive identification information from the sensor to uniquely identify the sensor.

6. The monitor of claim 4, wherein the second value is associated with the type of the sensor or with the individual sensor communicatively coupled to the monitor.

7. The monitor of claim 6, wherein the one or more sets of instructions retrieve the second value based on the identity of the type of the sensor or the individual sensor.

8. The monitor of claim 1, wherein determining the physiological parameter comprises determining a percent saturation of oxygen in hemoglobin.

9. The monitor of claim 1, wherein the second value is stored within the memory device of the monitor or within a second memory device coupled to the sensor.

10. The monitor of claim 1, wherein the one or more sets of instructions receive a coded value from the sensor associated with the second value.

11. A system, comprising:
a sensor configured to be disposed on a tissue of interest, the sensor comprising:
an emitter configured to emit electromagnetic radiation to the tissue of interest;
a detector configured to detect the electromagnetic radiation and generate a signal representative of a first amount of electromagnetic radiation detected by the detector;
and a monitor communicatively coupled to the sensor, the monitor comprising:
a first memory device comprising one or more tangible, non-transitory, machine readable media collectively storing one or more sets of instructions; and
a processing device configured to execute the one or more sets of instructions to:
receive the signal generated by the detector representative of the first amount of electromagnetic radiation detected by the detector;
retrieve a first value representative of a total amount of electromagnetic radiation emitted by the emitter;
retrieve a second value representative of a first attenuation coefficient, wherein the first attenuation coefficient is representative of attenuation excluding the tissue of interest, and wherein the first attenuation coefficient relates at least in part to a second amount of electromagnetic radiation shunting through the sensor;
determine a third value based at least in part on the first value, the second value, and the first amount of electromagnetic radiation, wherein the third value is a second attenuation coefficient representative of the tissue of interest; and
determine a physiological parameter based at least in part on the third value.

12. The system of claim 11, wherein the sensor comprises a second memory device comprising one or more tangible, non-transitory, machine readable media.

13. The system of claim 12, wherein the one or more sets of instructions store the first value or the second value within the first memory device or the second memory device.

14. The system of claim 13, wherein the one or more sets of instructions retrieve the first value or the second value from the second memory device.

15. The system of claim 11, wherein the one or more sets of instructions retrieve the first value or the second value from the first memory device.

16. The system of claim 11, wherein the sensor is configured to transmit coded values to the monitor representative of the first value or the second value.

17. The system of claim 11, wherein the sensor is configured to transmit sensor identification information to the monitor, and wherein the sensor identification information comprises a type of sensor.

18. The system of claim 17, wherein the one or more sets of instructions receive the sensor identification information and assign an identity to the sensor.

19. The system of claim 18, wherein the one or more sets of instructions retrieve the first value or the second value based on the identity of the sensor.

20. A method, comprising:
retrieving a first value from a memory device associated with a monitor or a sensor communicatively coupled to the monitor, wherein the first value is representative of a total amount of light emitted by an emitter when the sensor is applied to a tissue of interest associated with the sensor;
receiving a signal generated by a detector associated with the sensor, wherein the signal is representative of a first amount of light detected by the detector;
retrieving a second value from the memory device, wherein the second value is a first attenuation coefficient representative of background attenuation other than by the tissue of interest, and wherein the first attenuation coefficient relates at least in part to a second amount of light shunting through the sensor;
determining a third value based in part on the first value and second value by canceling the second amount of light shunting through the sensor from the first amount of light detected by the detector, wherein the third value is a second attenuation coefficient representative of the tissue of interest; and
determining a physiological parameter based at least in part on the third value.

* * * * *